(12) United States Patent
Gordon et al.

(10) Patent No.: US 11,266,829 B2
(45) Date of Patent: Mar. 8, 2022

(54) UNIVERSAL POWER SUPPLY FOR A FUNCTIONAL CRANIAL IMPLANT

(71) Applicant: Longeviti Neuro Solutions LLC, Hunt Valley, MD (US)

(72) Inventors: Chad R. Gordon, Cockeysville, MD (US); Jesse Christopher, Hunt Valley, MD (US); Corbin Clawson, Hampstead, MD (US); Jimmy Shah, Hunt Valley, MD (US)

(73) Assignee: LONGEVIT NEURO SOLUTIONS LLC, Hunt Valley, MD (US)

( * ) Notice: Subject to any disclaimer, the term of this patent is extended or adjusted under 35 U.S.C. 154(b) by 112 days.

(21) Appl. No.: 16/590,930

(22) Filed: Oct. 2, 2019

(65) Prior Publication Data

US 2020/0101281 A1    Apr. 2, 2020

Related U.S. Application Data

(60) Provisional application No. 62/740,106, filed on Oct. 2, 2018.

(51) Int. Cl.
| | | |
|---|---|---|
| *A61N 1/378* | (2006.01) | |
| *A61N 1/05* | (2006.01) | |
| *A61N 1/36* | (2006.01) | |
| *H02J 7/02* | (2016.01) | |
| *A61N 1/375* | (2006.01) | |

(52) U.S. Cl.
CPC ....... *A61N 1/0539* (2013.01); *A61N 1/36064* (2013.01); *A61N 1/378* (2013.01); *A61N 1/3787* (2013.01); *A61N 1/37514* (2017.08); *H02J 7/025* (2013.01)

(58) Field of Classification Search
CPC ... A61N 1/0539; A61N 1/37514; A61N 1/378
See application file for complete search history.

(56) References Cited

U.S. PATENT DOCUMENTS

| | | | |
|---|---|---|---|
| 4,206,762 A | 6/1980 | Cosman | |
| 5,443,504 A * | 8/1995 | Hill | ..... A61M 60/882 623/3.12 |
| 6,618,623 B1 | 9/2003 | Pless et al. | |
| 7,346,391 B1 * | 3/2008 | Osorio | ..... A61B 5/076 607/2 |
| 2005/0004620 A1 * | 1/2005 | Singhal | ..... A61N 1/3605 607/45 |
| 2014/0094674 A1 | 4/2014 | Nurmikko et al. | |
| 2014/0350635 A1 | 11/2014 | Strother et al. | |
| 2015/0223719 A1 | 8/2015 | Wahlstrand | |
| 2015/0289980 A1 | 10/2015 | Hirata et al. | |
| 2017/0224990 A1 | 8/2017 | Goldwasser et al. | |
| 2018/0055640 A1 | 3/2018 | Gordon et al. | |
| 2018/0085573 A1 * | 3/2018 | Alam | ..... A61N 1/36096 |
| 2018/0338835 A1 | 11/2018 | Gordon | |
| 2019/0209328 A1 | 7/2019 | Christopher et al. | |

* cited by examiner

*Primary Examiner* — Eric D. Bertram
(74) *Attorney, Agent, or Firm* — Welsh Flaxman & Gitler LLC (57) ABSTRACT

A low-profile intercranial device with universal power supply includes a static cranial implant adapted for the selective integration of a functional neurological implant. It also includes a universal power supply having a universal implantable power source with a connector.

12 Claims, 8 Drawing Sheets

UNIVERSAL POWER SUPPLY FOR A FUNCTIONAL CRANIAL IMPLANT

CROSS REFERENCE TO RELATED APPLICATION

This application claims the benefit of U.S. Patent Application Publication No. 62/740,106, entitled "UNIVERSAL POWER SUPPLY FOR A FUNCTIONAL CRANIAL IMPLANT," filed Oct. 2, 2018.

BACKGROUND OF THE INVENTION

1. Field of the Invention

The present invention relates to a universal power supply for a functional cranial implant.

2. Description of the Related Art

Fabricating a power supply for a functional cranial implant can be as complicated as actually designing the implant itself or the functional neurological implant mounted therein. With this in mind, the present invention provides a universal power supply specifically adapted for use in conjunction with a wide variety of functional cranial implants.

SUMMARY OF THE INVENTION

In an embodiment, a low-profile intercranial device with universal power supply includes a static cranial implant and a universal power supply. The universal power supply includes a universal implantable power source with a connector adapted for connection to a functional neurosurgical implant.

In another embodiment, a system for remote powering of a functional neurosurgical implant includes a static cranial implant housing a power supply and a functional neurosurgical implant. The power supply includes an implantable power source and a wireless charging system. The functional neurosurgical implant is in communication with the wireless charging system for powering the functional neurosurgical implant.

Other advantages of the present invention will become apparent from the following detailed description when viewed in conjunction with the accompanying drawings, which set forth certain embodiments of the invention.

DESCRIPTION OF THE PREFERRED EMBODIMENTS

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

With reference to the various embodiments disclosed below with reference to FIGS. 1 to 9, a low-profile intercranial device with a universal power supply is disclosed. In accordance with one embodiment disclosed with reference to FIGS. 1 to 5, 6A and 6B, the low-profile intercranial device 10, 10' with a universal power supply 12, 12' includes a static cranial implant 14 adapted for the selective integration of a functional neurological implant 16, 16' therein. In accordance with another embodiment disclosed with reference to FIG. 7 the low-profile intercranial device 110 includes a universal power supply 112 housed within a static cranial implant 114 of an intercranial assembly 111, while the functional neurological implant 116 is housed within a mounting plate 150 of the intercranial assembly 111. In accordance with yet another embodiment as disclosed with reference to FIGS. 8 and 9, the low-profile intercranial device 210 with a universal power supply 212 includes a static cranial implant 214 adapted for interaction with a functional neurological implant 216, 216' which is located external to the static cranial implant 214 which contains the universal power supply 212; that is, the static intercranial implant 212 contains only the universal power supply 212 and is electrically connected to a functional neurological device 216, 216' which is part of a separate and distinct intercranial device 214' or is directly implanted into the body (e.g., a microchip implanted directly within the skull).

As is explained below in greater detail, the universal power supply of the present invention is adapted for using in conjunction with a wide array of functional neurological devices. In accordance with one embodiment, this is achieved by providing a power source with a power output profile standardized for use in conjunction with a wide array of functional neurological devices through interconnection via industry standard wired connections or industry standard wireless power transfer protocols (for example, via inductive coupling or capacitive coupling).

As used within this disclosure, the term "intercranial" means situated or occurring within the cranium itself such that such devices are positioned within the space existing between the inner surface of the scalp and the outer surface of the dura. As such, intercranial devices are those devices intended for positioning within the cranium itself as opposed to devices that may be positioned on or adjacent to the cranium or positioned along the interior of the cranium, for example, between the cerebral cortex and the interior surface of the cranium. With this in mind, intercranial devices such as those discussed below replace resected portions of the cranium due to abnormalities in the cranium, damage to the cranium, or other medically sufficient reasons for resecting portions of the cranium.

As those skilled in the art will appreciate, it is often desirable that "intercranial" implants have the exact thickness and width, and/or shape and contour to replace all bone missing, as a method to avoid three suboptimal sequelae including 1) prevent dead space underneath (if the implant was thinner than missing bone), 2) causing inadvertent and detrimental pressure on the scalp above if and when the implant went beyond the outer cortex limits of the missing bone (if the implant was thicker than missing bone), and 3) causing inadvertent and detrimental pressure on the dura/brain underneath if and when the implant went beyond the inner cortex limits of the missing bone (if the implant was thicker than missing bone). Such "intercranial" implants have three potential indications for use including either replacing bone which has already been removed previously (at a previous surgical date, known as delayed cranioplasty), replacing diseased bone at time of surgical resection (referred to as single-stage cranioplasty), or replacing normal bone and simply being used for its inherent function and universal power supply. Furthermore, the term "intercranial" is opposed to devices that may be positioned on or adjacent to the cranium or positioned along the interior of the cranium, for example, between the cerebral cortex and the interior surface of the cranium.

The term "static" is used in the description of the present invention because the static cranial implant 14, has no encapsulated inner working (i.e., "functional") parts, batteries, wires, or computers, and is essentially an improved "empty-shell" which optimizes the inter-implant positioning within the confines of the skull and the neighboring functional neurosurgical implant 16.

The static cranial implant 14 of the present invention is preferably a low-profile static cranial implant 14 as described in Applicant's own U.S. Patent Application Publication No. 2018/0055640, entitled "METHOD FOR MANUFACTURING A LOW-PROFILE INTERCRANIAL DEVICE AND THE LOW-PROFILE INTERCRANIAL DEVICE MANUFACTURED THEREBY," filed Aug. 4, 2017, and PCT Publication No. WO 2017/039762, entitled "LOW-PROFILE INTERCRANIAL DEVICE," filed May 2, 2016, which are incorporated herein by reference. The static cranial implant 14 is, therefore, designed for maximal interdigitating of the static cranial implant 14 with a functional neurosurgical implant 16 to be selected based upon the specific needs of the patient. The term "interdigitating" is meant to refer to the interlocking of two distinct elements (that is, the static cranial implant 14 and the functional neurosurgical implant 16) such that the two distinct elements mesh together to ultimately define a single product. It is appreciated that while the various embodiments disclosed herein only show a single functional neurosurgical implant 16 in conjunction with a static cranial implant 14, multiple functional neurosurgical implants 16 may be used in a single static cranial implant 14 in accordance with the present invention. The static cranial implant 14 is adapted for ideal functional and aesthetic benefits, thereby minimizing unnecessary spaces, inter-implant gaps, and sharp irregular angles. This helps to minimize risk of scalp pain, visible deformity, and implant micromotion—all of which often leads to treatment failure and surgical explantation (that is, premature removal of the implant).

As briefly mentioned above, the low-profile intercranial device 10 with a universal power supply 12 includes a universal power supply 12 integrated with the static cranial implant 14. As will be explained below in greater detail, the static cranial implant 14 is formed with a power supply recess 18 (and associated passageways) adapted for the placement of the universal power supply 12 within the static cranial implant 14. As with the incorporation of the functional neurological implant 16 into the static cranial implant 14, the power supply recess 18 is formed to provide for maximal interdigitating of the static cranial implant 14 with the universal power supply 12.

In order to achieve ideal fit amongst the static cranial implant 14, the functional neurological implant 16 and the universal power supply 12, the static cranial implant 14 of the present invention employs a CT (Computed Tomography) scan-based, virtual design session performed pre-operatively based on the brain-specific geographical location (as opposed to the standard method of using the skull-specific geographic location) in the manufacture of the low-profile intercranial device 10. In addition, a plain X-ray or MRI (Magnetic Resonance Imaging) would fail to provide enough bone data for manufacturing and designing this type of intercranial implant. As a result, and for the first time, the methodology employed in accordance with the present invention accommodates both brain and skull pathology in three-dimensional space, in all three axes, prior to surgery.

With this information, as well as knowledge regarding the dimensions of the functional neurosurgical implant 16 and universal power supply 12, the static cranial implant 14 is produced. The static cranial implant 14 is augmented, reduced and/or modified to include a cavity 20 for the functional neurosurgical implant 16. It is appreciated multiple cavities may be employed where the functional neurosurgical implant(s) 16 being used dictates and that the cavity 20 need not be directly in the center of the static cranial implant 14 but may be offset as dictated by the procedure being performed. The static cranial implant 14 is also augmented, reduced and/or modified to include other structural elements 22 (for example, wire tunnel(s), pocket(s), etc.), shaped and dimensioned for optimal anatomical placement of the functional neurosurgical implant 16 that is ultimately positioned within the confines of the cavity 20 (and other structural element(s)) of the static cranial implant 14 (i.e., like an empty shell case but with exact negative and positive enhancements to optimize anatomical positioning of both the static cranial implant 14 and the functional neurosurgical implant 16).

The static cranial implant 14 is also augmented, reduced and/or modified to include the power supply recess 18 for the universal power supply 12 (it is appreciated multiple recesses may be employed where the universal power supply(ies) 12 being used dictates), as well as other structural elements 24 (for example, wire tunnel(s), pocket(s), etc.), shaped and dimensioned for optimal anatomical placement of the universal power supply 12 that is ultimately positioned within the confines of the power supply recess 18 (and other structural element(s)) of the static cranial implant 14 (i.e., like an empty shell case but with exact negative and positive enhancements to optimize anatomical positioning of both the static cranial implant 14 and the universal power supply 12).

Depending upon the specifics of the functional neurosurgical implant 16 and the universal power supply 12 positioned within the cavities 18, 20 of the of static cranial implant 14, various mechanical coupling mechanisms, for example, screws, plates, etc. (not shown), are used to ensure that the functional neurosurgical implant 16 and the universal power supply 12 are securely held in place. As will be explained below in greater detail, the manufacture of the low-profile intercranial device 10 utilizes computer-based designs and modeling (CAD/CAM) of both the static cranial implant 14, the functional neurosurgical implant 16, and the universal power supply 12.

The computer-based designs of the static cranial implant 14, the functional neurosurgical implant 16, and the universal power supply 12 are optimized in the manner described in Applicant's own U.S. Patent Application Publication No. 2018/0055640, entitled "METHOD FOR MANUFACTURING A LOW-PROFILE INTERCRANIAL DEVICE AND THE LOW-PROFILE INTERCRANIAL DEVICE MANUFACTURED THEREBY," filed Aug. 4, 2017, and PCT Publication No. WO 2017/039762, entitled "LOW-PROFILE INTERCRANIAL DEVICE," filed May 2, 2016, which are incorporated herein by reference.

Briefly, and as will be appreciated based upon the following disclosure, the static cranial implant 14 of the present invention is a modified version of a low-profile cranial implant commonly used and known by those skilled in the art of cranial surgical procedures. Such implants may take a variety of forms and are most commonly shaped and dimensioned for integration into the structure of a patient's skull; that is, the static cranial implant 14 has a geometry that substantially conforms to a resected portion of the patient's anatomy to which the implant is to be secured. Briefly, the static cranial implant 14 of the present invention includes an outer (commonly convex) first surface 14o, an inner (commonly concave) second surface 14i, and a peripheral edge 14p extending between the outer first surface 14o and the inner second surface 14i. The static cranial implant 14 is shaped and dimensioned for engagement with the skull of the patient upon implantation in a manner well known to those skilled in the field of neurosurgical procedures. The outer first surface 14o and inner second surface 14i of the static cranial implant 14 are preferably curved in a superior to inferior direction, a posterior to anterior direction, and a medial to lateral direction. In addition, the peripheral edge 14p has a substantial taper for resting upon a matching taper formed along the skull. It is, however, appreciated that this taper may vary (or not exist at all, that is, the peripheral edge 14p may be substantially perpendicular relative to the outer first surface 14o and the inner second surface 14i) depending upon the specific needs of the procedure.

In accordance with a preferred embodiment, the static cranial implant 14 has a preselected thickness not exceeding the space between the inner surface of the scalp and the outer surface of the dura, for example, in the range of around 1 millimeter to 25 millimeters (with areas of strategic bulking and/or thinning) and depending upon the strength of the materials used in the construction of the static cranial implant 14. Preferably, the static cranial implant 14 will have a thickness of 1 millimeter to 12 millimeters. These lower and upper limits are of significance. One millimeter is the smallest thickness for which most alloplastic materials can remain protective of the brain related to tensile strength, one example being poly-methyl-methacrylate. Twelve millimeters is the estimated size for which one should consider abnormal impingement of the underlying brain, for which may cause pressure-related paralysis upon the motor cortex of the brain.

As mentioned above, the static cranial implant 14 also includes a cavity 20 (for example, formed along the inner surface) and optional structural elements 22, for example, channels, pockets, access holes, and/or other structural elements, designed to accommodate various features of the functional neurosurgical implant 16. In the disclosed embodiment, structural elements 22 in the form of channels are provided. The channels 22 have a first end 22a in communication with the cavity 20 and a second end 22b extending to the inner second surface 14i of the static cranial implant 14 for the passage of electrodes of the functional neurosurgical implant 16 for applying stimulation to the brain. Since many functional neurosurgical implants 16 interact with a control device (not shown) via wireless mechanisms, access between the outer first surface 14o (or top surface) and the center cavity 20 may not be required, although it is appreciated channels or other structural elements 22 could certainly be provided for external contact as needed.

As is also mentioned above, the static cranial implant 14 also includes a power supply recess 18 (for example, formed along the inner surface) and optional structural elements 24, for example, channels, pockets, access holes, and/or other structural elements, designed to accommodate various features of the universal power supply 12, and connections between the universal power supply 12 and the functional neurosurgical implant 16. In the disclosed embodiment, structural elements 24 in the form of channels are provided.

In accordance with a first embodiment, and as briefly discussed above, the universal power supply 12 includes a universal implantable power source 30 with a standard (or proprietary) wired connector 32 for connection of the power source 30 with the functional neurosurgical implant 16 (via wires 29 extending between the universal power supply 12 and the functional neurosurgical implant 16) so as to provide power thereto. The power source 30 has a power output profile standardized for use in conjunction with a wide array of functional neurological devices and includes an industry standard connector.

Figure 1:
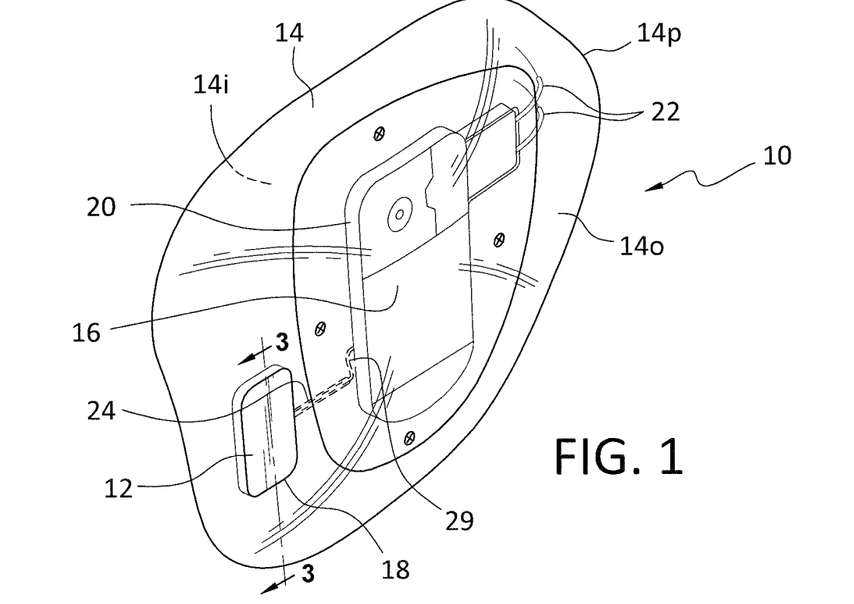
FIG. 1 is a perspective view of a low-profile intercranial device with a universal power supply.
Figure 2:
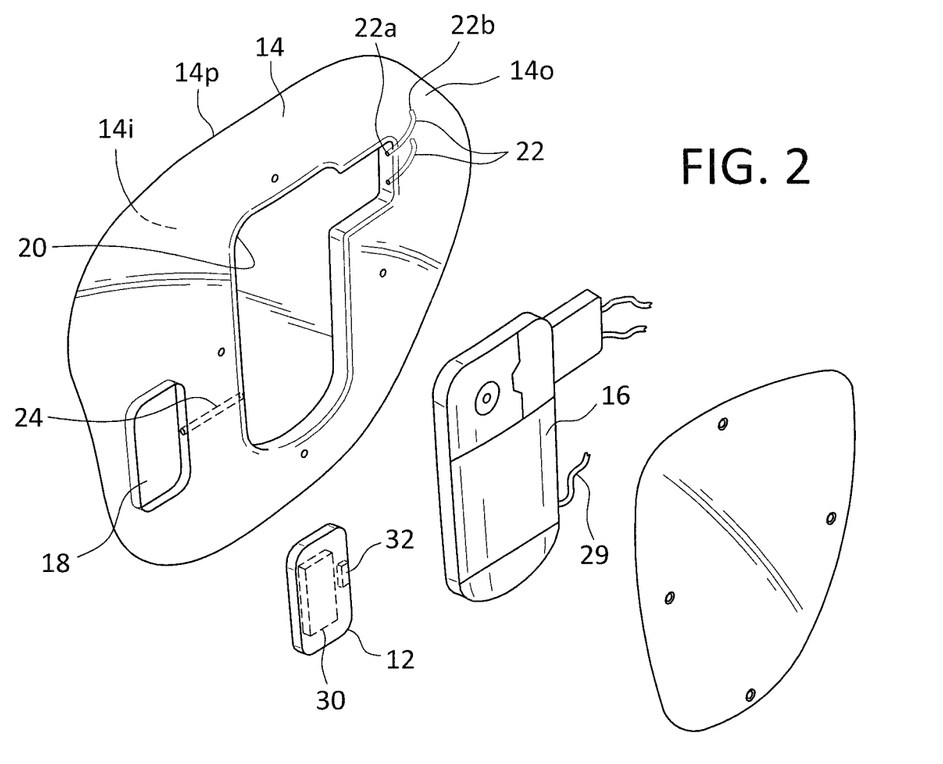
FIG. 2 is an exploded view of the low-profile intercranial device with a universal power supply as shown in FIG. 1.
Figure 2A:
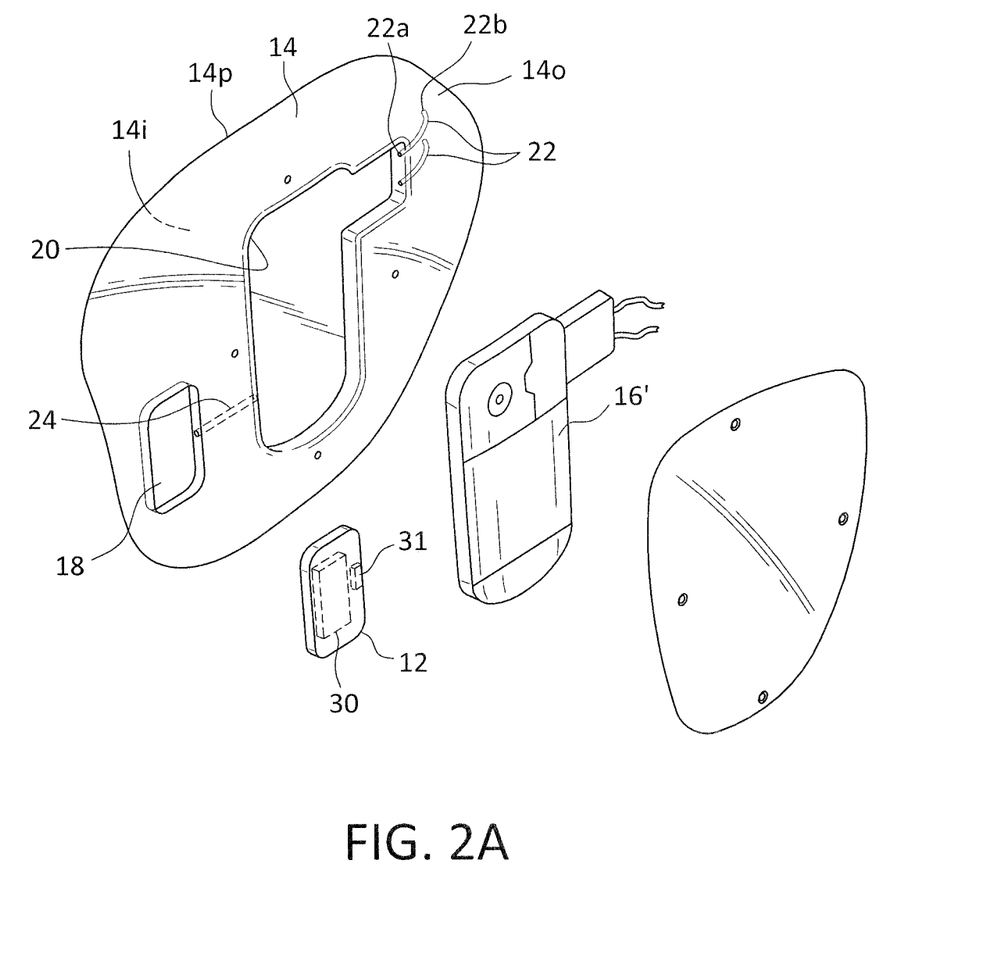
FIG. 2A is an exploded view of the low-profile intercranial device with a universal power supply in accordance with an alternate embodiment.
Figures 3, 4:
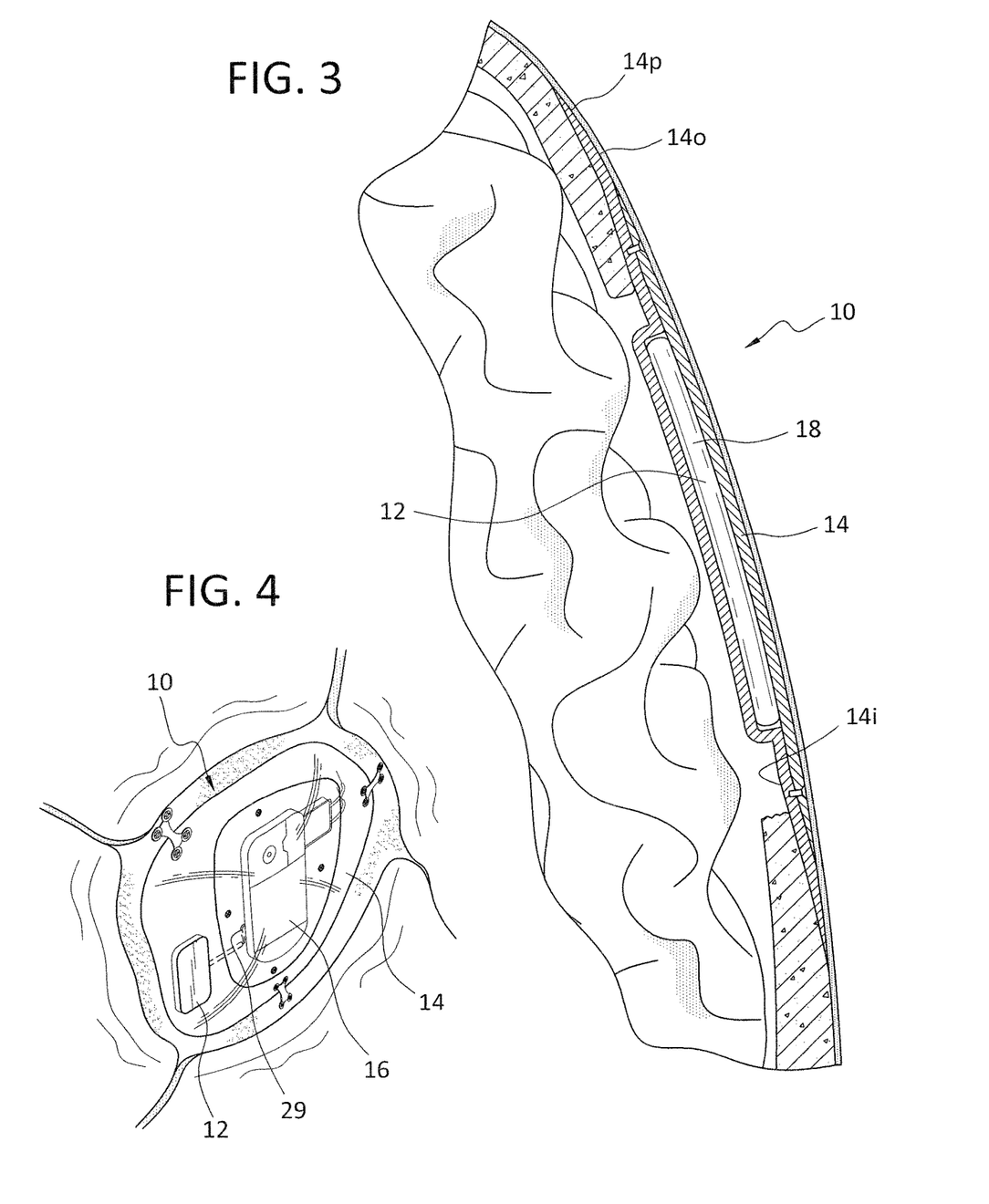
FIG. 3 is a cross sectional view of the low-profile intercranial device with a universal power supply along the line 3-3 in FIG. 1 and installed within the cranium of a patient.
FIG. 4 is a perspective view of the low-profile intercranial device with a universal power supply installed within the cranium of a patient.

In accordance with an alternate embodiment as shown with reference to FIG. 2A, the universal power supply 12 may include a wireless communication and/or charging system 31 (for example, a wireless communication and/or charging system employing standard wireless power transfer protocols (for example, via inductive coupling or capacitive coupling)), alone or in conjunction with the standard connector 32 discussed above. Such a wireless communication and/or charging system 31 functions in conjunction with a functional neurosurgical implant 16', which has been designed to allow for wireless electrical power transfer thereto, to provide for the wireless transfer of electrical power from the universal power supply 12 to the functional neurosurgical implant 16.

Through the provision of such a universal power supply 12, specific medical devices that require power will have a known standard to employ for the baseline of the design. For example, if one were to develop a brain stimulator, he/she would take the present universal power supply 12 into consideration as he/she designed the brain simulator. Therefore, the brain simulator would be designed to function in a "plug and play" manner with the universal power supply so as to reduce the regulatory and engineering burden on the stimulator development.

The power source 30 may take the form of a lithium-ion battery, a solid-state battery, a microbiology battery, a glucose powered system, or a piezoelectric battery. Such batteries as are preferably rechargeable through mechanisms known to those skilled in the art. The power source could also take the form of malleable solid-state batteries. Still further, the universal power supply could be constructed such that batteries and components making up the power source are housed through a process in which they are suspended and fully encapsulated (for example, like a fossil in sap) or built around with a top and bottom enclosure (that is, sandwiched). Such a sandwich process will allow later replacement of batteries, indefinitely. It is also contemplated, the power source might take the form of a perpetual battery run by kinetic energy (for example, like the automatic mechanical systems employed in various watches, for example, a Rolex® watch). For the purposes of disclosure, the terms "battery" or "batteries" is used below interchangeably with the term power source when describing various embodiment of the present invention. In accordance with such an embodiment, the power source provides an output voltage that can be a multiple of the nominal voltage of the cells of the power source. If a voltage regulation device is used as discussed below, the output voltage can be amplified to any value to meet the power demands of the functional device.

As to the wired connector 32, it will take the form of a universally accepted form, for example, Lightning connector, USB connector, other connector structures well known to those skilled in the art. With 3-D printing, it is further appreciated the connection to the functional neurosurgical implant could be achieved via soldering, laser welding or other mechanisms for hardwiring of the power source to the functional neurosurgical implant.

Regardless of whether the universal power supply disclosed with reference to FIGS. 1, 2, 3 and 4 or with reference to FIG. 2A is employed, it is appreciated the universal power supply could include multiple batteries as the power source 30.

Figure 5:
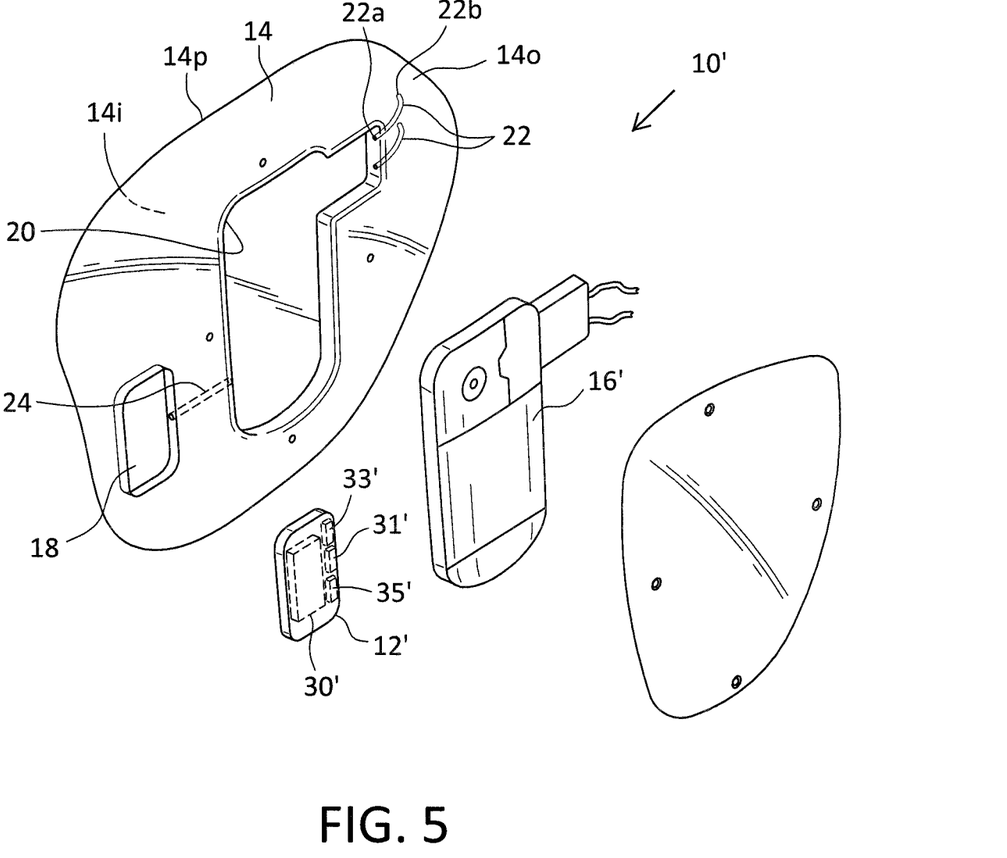
FIG. 5 is an exploded view of the low-profile intercranial device with a universal power supply in accordance with another embodiment.
Figure 6A:
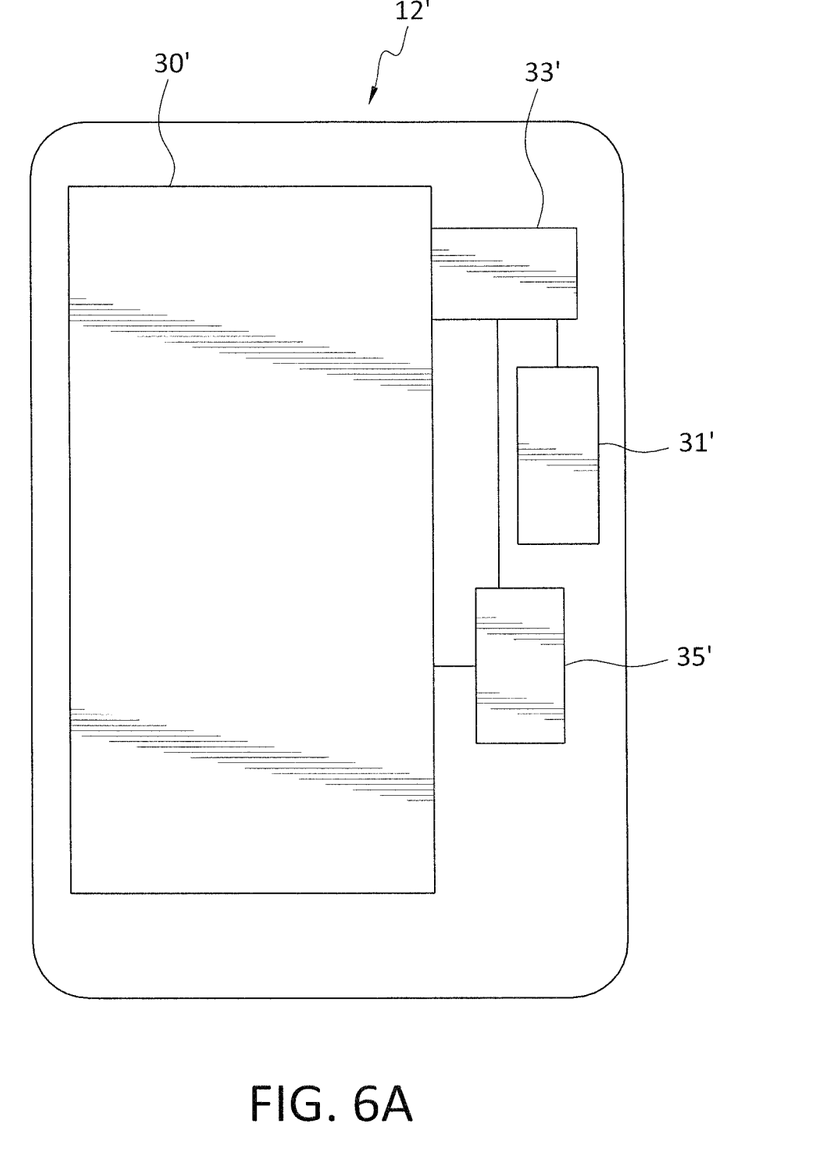
FIGS. 6A and 6B are schematics of embodiments of the universal power supply that may be used in conjunction with the embodiment shown in FIG. 5.
Figure 6B:
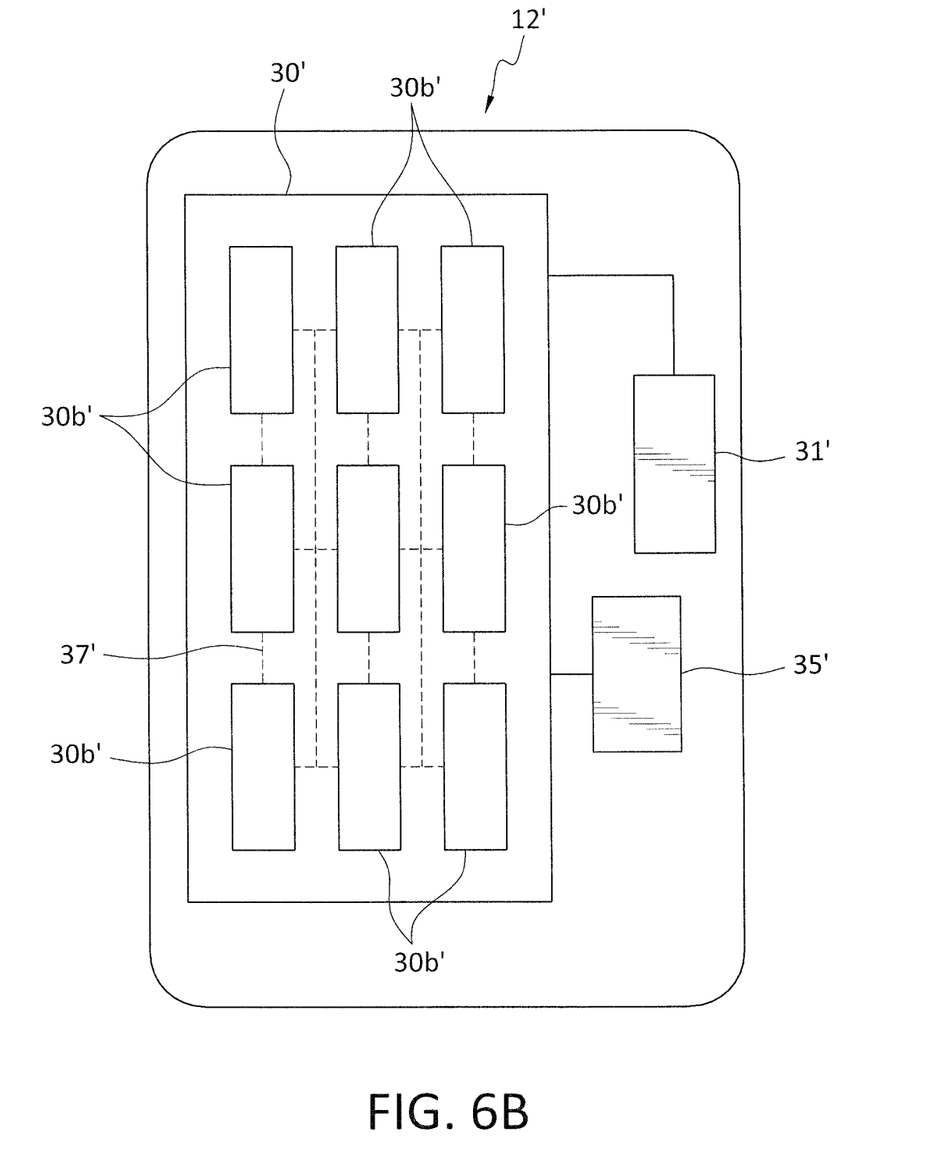

In accordance with an alternate embodiment, as shown with reference to FIGS. 5, 6A, and 6B, the universal power supply 12' is a variable power device accommodating various power demands. The power supply 12' includes an output control system 33' integrated with the implantable power source 30' for selectively adjusting the output of the universal power supply 12' to accommodate the needs of the functional neurosurgical implant 16'. As with the prior embodiment, such a universal power supply 12' would include a wired connector 32 and/or a wireless communication and/or charging system 31 (please note the wireless communication and/or charging system 31' is shown in FIGS. 5, 6A, and 6B, although it is appreciated wireless or wired electrical power transfer could be used, alone or in combination, in accordance with the present embodiment).

In accordance with a first embodiment of the universal power supply 12' adapted to accommodate various power demands, and as shown in detail with reference to FIG. 6A, the output control system 33' is an adjustable voltage regulator (or controller). Such voltage regulators (or controllers) are known in the art and are composed of variable resistors, diodes, transistors, operational amplifiers, switches, or combinations of such components. The voltage regulator (or controller) 33' is used to maintain a specified input voltage to the functional neurosurgical implant 16', which has been designed to allow for wireless electrical power transfer thereto, to ensure the functional neurosurgical implant 16' will function properly. If the functional neurosurgical implant 16' were to unexpectedly draw excessive current, the voltage regulator (or controller) 33' is provided with a safety and protection mechanism to prevent the functional neurosurgical implant 16' from damaging itself or harming the patient.

In addition to the voltage regulator (or controller) 33', the output control system 33' also includes a power management system 35' integrated with the universal power supply 30' to control the voltage regulator (or controller) 33' and, thereby, manage the power delivery and charging of the power source 30', for example, implanted battery(ies). The power management system 35' is able to receive information, either wirelessly or by direct connection, about the power needs of the functional neurosurgical implant 16' in order to deliver appropriate power. For example, it is contemplated the power management system 35' could interrogate the functional neurosurgical implant 16 to determine the power requirements thereof and subsequently adjust the power output to accommodate the specific needs of the functional neurosurgical implant 16'. Further, it is also contemplated the power management system 35' could interrogate the functional neurosurgical implant 16' to ensure compatibility and provide a warning where, for whatever reasons, the power source is not compatible with the functional neurosurgical implant.

The power management system 35' is also able to transmit information, either wirelessly or by direct connection, about the state of the battery(ies) 30' and supply of power to the functional neurosurgical implant 16' (or to an external receiver). The power management system 35' also controls the power output and power input to and from the battery(ies) 30' for the purposes of providing power to the functional neurosurgical implant 16' or charging the battery(ies) 30'.

As discussed above, the universal power supply is contemplated to include an implantable power source composed of multiple batteries as the power source. Where multiple batteries 30b' are used as the implantable power source 30', and with reference to FIG. 6B, the configuration of the batteries 30b' can be customized to achieve desired power characteristics and thereby provide an another embodiment for the provision of a variable power device accommodating various power demands. By altering the batteries' configuration from series to parallel, or any combination thereof, the capacity and output voltage of the batteries 30b' can be tailored to meet the demands of the functional neurosurgical implant 16'. It is appreciated the configuration of the batteries 30b' can be changed wirelessly on-demand through the use of a power management system 35' controlling circuit switching components and circuits 37', for example, through the integration of electromechanical regulators that wirelessly open and close circuits so as to alter the battery configuration.

As with the embodiment discussed above, and as briefly discussed above, the power management system 35' is integrated with the implantable power source 30' to manage the power delivery and charging of the implanted batteries 30b'. The power management system 35' is able to receive information, either wirelessly or by direct connection, about the power needs of the functional neurosurgical implant 16' in order to deliver appropriate power. For example, it is contemplated the power management system 35' could interrogate the functional neurosurgical implant 16 to determine the power requirements thereof and subsequently adjust the power output to accommodate the specific needs of the functional neurosurgical implant 16'. Further, it is also contemplated the power management system 35' could interrogate the functional neurosurgical implant 16' to ensure compatibility and provide a warning where, for whatever reasons, the power source 30' is not compatible with the functional neurosurgical implant 16'.

The power management system is also able to transmit information, either wirelessly or by direct connection, about the state of the batteries 30b' and power supply to the functional neurosurgical implant 16' or to an external receiver. The power management system also controls the power output and power input to and from the batteries 30b' for the purposes of providing power to the functional neurosurgical implant 16' or charging the batteries.

By altering the batteries' configuration under the control of power management system 35' it is possible to selectively provide higher voltage by configuring batteries 30b' in series or higher current and capacity by configuring batteries 30b' in parallel. Further still, through the use of multiple batteries 30b' it is possible to address long-term patient needs. For example, if a functional neurosurgical implant 16' intended to be implanted for an extended length of time only requires one battery to functional properly, additional back-up batteries can remain idle within the static cranial implant 14 until their needs are called upon. This allows, for example, through the integration of electromechanical regulators that wirelessly open and close circuits as discussed above, old, spent batteries to be wirelessly disconnected from the circuit while the idle, fresh batteries are integrated into the circuit without the need for surgical intervention, thus extending the lifespan of the universal power supply.

In accordance with a preferred embodiment, the cranial implant 14 is fabricated from a wide array of commonly-available biomaterials including, but not limited to, clear and/or opaque PMMA (Poly(methyl methacrylate)), PEEK (Polyether ether ketone), PEKK (Polyetherketoneketone), porous polyethylene, titanium alloy, bone allograft, bone autograft, bone xenograft, and/or various other tissue-engineered bone constructs. In accordance with one embodiment, the static cranial implant 14 is ideally made of clear PMMA since it's fully lucent and transparent. This allows for novel inspection of the interdigitated functional neurosurgical implant 16 and neighboring components. As will be explained below in greater detail, it also allows for the critical transmission of vital imaging with minimal distortion, such as ultrasound waves for brain pathology detection, and wireless signal communication (i.e., electroencephalography or ECOG)—essential for various neuromodulation devices such as NeuroPace®, for example—as first described by Gordon et al. in *Operating Surgery* in 2017 (full citation below). Another clear material that may be readily used in accordance with the present invention is cubic zirconium. While clear material is disclosed in accordance with a preferred embodiment, it is appreciated the underlying concepts of the present invention may be achieved through the utilization of an opaque static cranial implant 14.

The optical clarity of the static cranial implant 14 is important in expanding the potential uses of the low-profile intercranial device 10 and in expanding the potential functional neurosurgical implants 16 that may be used in conjunction with the present invention. For example, the provision of high optical clarity allows for wireless optical links between the functional neurosurgical implants 16 and remote devices or between functional devices on the interior of the cranium and the exterior of the low-profile intercranial device 10 (for example, transmitting between the cortex and the other side of the low-profile intercranial device). Enhanced optical clarity similarly allows for power transmission and/or receipt between the functional neurosurgical implants 16 and devices outside of the static cranial implant 14. Potential operations that may be achieved through the utilization of optical links through a high clarity static cranial implant 14 include, but are not limited to, device start-up, device calibration, and device operational control.

Still further, the static cranial implant 14 is constructed of a material allowing for imaging of the brain through the static cranial implant 14, for example, via ultra-sound. It is known that clear PMMA will provide the ability to permit ultra-sound imaging of the brain therethrough so long as it is manufactured without additives that might function to block the frequency and amplitude of the ultrasound transducer. In accordance with one embodiment, the static cranial implant 14 is ideally made of clear PMMA since it's fully translucent to light, sonolucent to ultrasound, radiolucent to ECOG signals (as first described by Gordon et al. in "First in-human experience with complete integration of neuromodulation device within a customized cranial implant." Operative Neurosurg 2017), and transparent for ideal visualization necessary for brain lead placement, catheter positioning, etc.

In addition to the optimal material choice, the preferred static cranial implant may be 3D printed, direct digital manufacturing, or a combination thereof. In this way necessary circuitry can be printed into or added to the implant at the optimal location(s) during the additive manufacturing process.

While a preferred static cranial implant 14 is disclosed in accordance with the present invention, the static cranial implant 14 used in conjunction with the present invention may take a variety of forms so long as the static cranial implant 14 includes a cavity 20 (and, optionally, other structural elements) configured to conform to the exact requirements of the functional neurosurgical implant 16 and a power supply recess 18 (and, optionally, other structural elements) configured to conform to the exact requirements of the universal power supply 12 in accordance with the present invention.

Based upon the functional neurosurgical implant 16 used in conjunction with the present invention, the functional neurosurgical implant 16 may be useful in the treatment of various patient conditions such as brain tumor management (drug delivery, remote image monitoring), hydrocephalus (flow monitor, ICP pressure sensors), epilepsy, movement disorders, chronic pain, spasticity, cerebral palsy, multiple sclerosis, spinal cord injury (with or without paralysis), traumatic brain injury, attention-deficit/hyperactivity disorder, autism, obsessive-compulsive disorders, etc. —and the potential to obtain supra-normal levels of brain function in both military and civilian situations for enhanced memory or physical activity. Furthermore, incorporation of imaging devices within cranial implants 14 could help to provide ongoing tumor bed monitoring for early detection of disease recurrence.

By way of example, one potential functional neurosurgical implant 16 that may be employed in accordance with the present invention is a battery-powered functional neurosurgical implant 16 known as the NeuroPace® device, that is, a device for responsive neurostimulation for epilepsy, which has a design flaw in that it limits the visible aesthetic result due to its irregular shape(s), causes undue pressure on the undersurface of the scalp, and suffers significant implant micromotion thereby leading to common device infection and bone flap osteomyelitis (See, Wei Z, Gordon C R, Bergey G K, Sacks J M, Anderson W S. Implant Site Infection and Bone Flap Osteomyelitis Associated with the NeuroPace Responsive Neurostimulation System. World Neurosurg 2015 Dec. 29; pii: s1878-8750(15)075-1.) These deficiencies are overcome in accordance with the present invention by optimizing the static cranial implant 14 for receipt of the NeuroPace® device and improving its rigid placement within the intercranial space.

With the foregoing in mind, additional functional neurosurgical implants 16 that may be used in conjunction with the present invention include, but are not limited to the following: Deep Brain Stimulators (DBS); Cortical Brain Stimulators (CBS); neurologic medicines that are otherwise prevented from diffusing through the blood-brain barrier via common delivery methods; battery, passively, kinetically, or otherwise-powered functional devices including neuromodulation devices, imaging devices, radiation therapy devices, and remote sensing/monitoring devices; monitoring devices for abnormal levels of intracranial pressure (ICP) or brain activity (i.e., seizures), such as an electrical array for motor/vision cortex control, battery/passively/kinetically/or otherwise-based stimulation hardware for epilepsy management (grids/batteries/wires); low-profile remote imaging devices (e.g., optical coherence tomography (OCT), duplex ultrasound); delivery/sensing devices for electrical impulses; neurological and physiological systems required for deep space/sleep functionalities enhancing the monitoring and/or maintenance of bodily vital signs, nutrition, cognition, etc.; convection enhanced delivery systems effectively delivering therapeutics to substantial volumes of brain and brain tumor; and remote neuro-imaging devices (i.e., electroencephalogram (EEG).

The functional neurosurgical implants 16 of the present invention may also incorporate high-precision and fully implantable next-generation neural interface systems taking advantage of microelectronics and photonics along with advances in scalable neural encoding and processing algorithms to demonstrate the transformation of high-definition sensory stimuli to and from sensory cortex areas, bridging physiological and electronic neural activity representations.

With this in mind, the term "functional neurosurgical implant" is meant to reference any therapeutic hardware or compositions including, but not limited to, medicines to treat any patient-specific illness, or electronic, mechanical, imaging modality and/or electro-mechanical device to remotely monitor (e.g., via Wi-Fi connectivity) or intervene any specific neurologic illness, including imaging, monitoring, electrostimulation, radiation therapy, polarized light/laser neuronal modulation devices. The term "functional" denotes the fact that these implants provide the low-profile intercranial device with the ability to function as more than a safe custom-shaped skull replacement by providing various functionalities, for example, local drug delivery, monitoring (such as brain monitoring), or local electric stimulation to the patient.

While the embodiment described above provides for a universal power supply 14 that is connected to a functional neurosurgical implant(s) 16 maintained within a unitary static cranial implant 14, an alternate embodiment is disclosed in FIG. 5 wherein the universal power supply 114 and the functional neurosurgical implant(s) 116 are maintained in different portions of the intercranial device 110. In such an embodiment, the intercranial device 110 is a multi-part intercranial assembly as disclosed in Applicant's own U.S. patent application Ser. No. 16/203,357 (published as US2019/0209328) entitled "UNIVERSAL LOW-PROFILE INTERCRANIAL ASSEMBLY," which is incorporated herein by reference.

Figure 7:
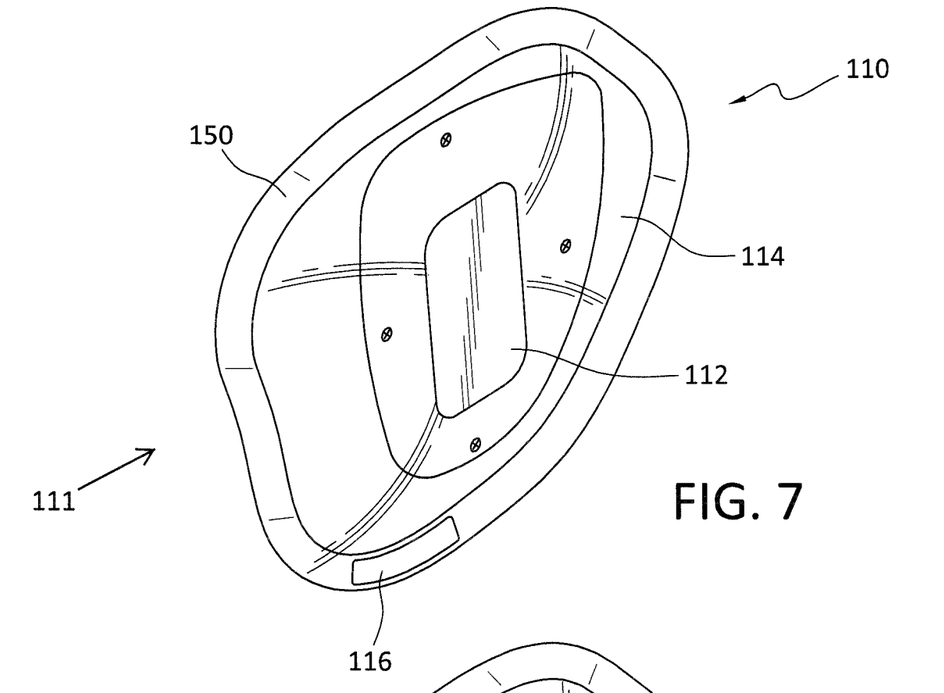
FIG. 7 is a perspective view of an embodiment of the low-profile intercranial device with a universal power supply.

In accordance with this embodiment, the universal power supply 112 is housed within the static cranial implant 114 of the intercranial assembly 110 and the functional neurosurgical implant(s) 116, which has been designed to allow for wireless electrical power transfer thereto, is housed within the mounting plate 150 intercranial assembly 110. Briefly, and as is disclosed in detail the '328 publication, the intercranial assembly 110 is composed of mounting plate 150 in which the functional neurosurgical implant(s) 116 is housed and a static cranial implant 114 in which the universal power supply 112 is housed. Through use of a static cranial implant 114 that may be selectively mounted and dismounted from the mounting plate 150, it is possible to easily replace the universal power supply 112 with removing, altering, or otherwise changing the properly positioned functional neurosurgical implant(s) 116.

As the universal power supply 114 and the functional neurosurgical implant(s) 116 are separately housed, and it is ultimately desirable to allow for removal of the universal power supply 114 with disrupting the functional neurosurgical implant(s) 116, the universal power supply 114 is adapted for wireless connection with the functional neurosurgical implant(s) 16 so as to provide power to the functional neurosurgical implant(s) 116. As such, it is preferred that the embodiment of the universal power supply as disclosed with reference to FIG. 2A be used with this embodiment, although it is appreciated a wired connection could also be used within the spirit of the present invention.

While the embodiments described above provides for a universal power supply that is connected to a functional neurosurgical implant(s) maintained within the same implant or implanted assembly, it is appreciate various other implementations are possible. For example, and with reference to FIGS. 8 and 9, it is contemplated that the intercranial device 210 composed of an intercranial implant with universal power supply contemplated by the present disclosure may take the form of an static cranial implant 214 containing only the universal power supply 212, and not the functional neurosurgical implant 216, 216'. In accordance with such an embodiment, the neurosurgical functional implant 216, 216', which has been designed to allow for wireless electrical power transfer thereto, is located external to the static cranial implant 214 which contains the universal power supply 212, such as in a separate static cranial implant 214' or directly implanted into the body (see FIG. 9).

In implementing such an embodiment, either the cranial implant of the embodiment disclosed with reference to FIGS. 1 to 4 or the multiple-part intercranial assembly disclosed with reference to FIG. 7 may be used to house the universal power supply 212. The multiple-part intercranial assembly 210 disclosed with reference to FIG. 7 is, however, shown in the disclosed embodiment as this allows for ready replacement of the universal power supply 212.

Figure 8:
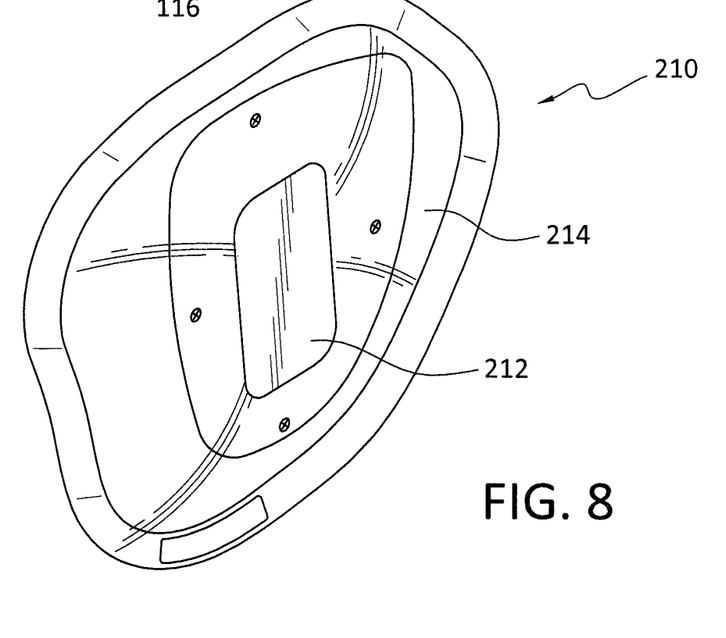
FIG. 8 is a perspective view of another embodiment of the low-profile intercranial device with a universal power supply.
Figure 9:
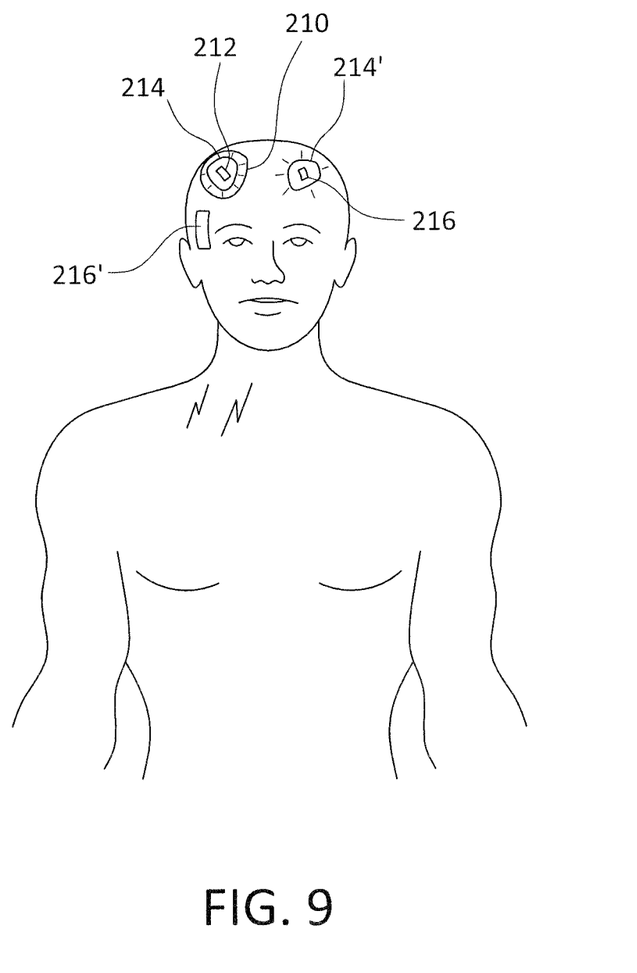
FIG. 9 is a schematic showing use of the low-profile intercranial device with a universal power supply.

Referring to FIGS. 8 and 9, the universal power supply 212 is housed within the static cranial implant 214 of the intercranial assembly 210. The functional neurosurgical implant(s) 216 may be housed within an alternate implant 214' (for example, a static cranial implant as described in Applicant's own U.S. Patent Application Publication No. 2018/0055640, entitled "METHOD FOR MANUFACTURING A LOW-PROFILE INTERCRANIAL DEVICE AND THE LOW-PROFILE INTERCRANIAL DEVICE MANUFACTURED THEREBY," filed Aug. 4, 2017, and PCT Publication No. WO 2017/039762, entitled "LOW-PROFILE INTERCRANIAL DEVICE," filed May 2, 2016, which are incorporated herein by reference. The functional neurosurgical implant(s) 216' may also be directly implanted into the body.

As with the embodiments disclosed with reference to FIGS. 2A, 5, 6A, and 6B, and considering the universal power supply 212 and the functional neurosurgical implant(s) 216, 216' are remotely positioned within the body, the universal power supply 212 is adapted for wireless connection with the functional neurosurgical implant(s) 216, 216' so as to provide power to the functional neurosurgical implant(s) 216, 216'. As such, it is preferred that the embodiment of the universal power supply as disclosed with reference to FIGS. 2A, 5, 6A, and 6B be used with this embodiment, although it is appreciated a wired connection could also be used within the spirit of the present invention.

Accordingly, the universal power supply 212 is contained in one intercranial implant 214 with the functional neurological implant 216 contained in a separate intercranial implant 214', that is, an intercranial implant that does not nest with or otherwise form a part of the intercranial implant 214 in which the universal power supply 212 is housed. In this manner, the universal power supply 212 may be implanted at one location and the functional neurosurgical device 216 may be implanted at a different location, which may be alongside the universal power supply 212 location or at a location separate from the universal power supply 212 location. Such a configuration may provide many advantages. For example, by separating the power supply 212 from the functional neurosurgical implant 216 the surgeon is provided greater flexibility in placing each device. It may be that the desired location for one or both of the universal power supply 212 and functional neurosurgical device 216 is not conducive to designing and implanting an implant containing both devices, and by separating the two to different locations, more suitable locations for each may be used. The two merely need to communicate to deliver power from the universal power supply 212 to the functional neurosurgical device 216.

Where the universal power supply and functional neurosurgical device are not mounted within the same implant, it is contemplated that it may not be necessary to employ a universal power supply to take advantage of concepts underlying the present invention. Rather a power supply may be specifically matched to operate in conjunction with the functional neurological device and remotely linked thereto to provide power for the operation of the functional neurological device.

As discussed above, it is further contemplated that the functional neurosurgical device 216' may be directly implanted into the body without being held in an intercranial implant. Thus, as microchip-based devices become more sophisticated and efficient, it may be possible to implant all or most of the functional neurosurgical device directly into the desired body tissue. By way of example, a microchip programmed to treat a disease or condition may be directly implanted into the brain, and powered by a universal power supply 212 implanted in the intercranial space as part of an intercranial device 210, with the universal power supply 212 communicating power (wired or wirelessly) to the directly implanted functional neurosurgical implant 216'.

By way of further example, the functional neurosurgical implant 216 may be a brain mapping device, with the brain mapping grid placed onto the brain and connected to the universal power supply 212. After mapping, it is also contemplated the mapping grid might be removed, and the universal power supply 212 connected to another functional neurosurgical implant in the form of a functional neurological treatment device such as an electrical stimulation device to provide treatment, with the treatment device implanted directly into the brain or in a separate intercranial implant.

It is also contemplated that the universal power supply 212 could be configured to deliver power to more than one functional neurosurgical device 216, 216' (see FIG. 9). Under such circumstances, implanting the universal power supply 212 and each functional neurosurgical device 216, 216' independent of each other provides flexibility in the location of each and the access and replacement of one device independent of the others.

In the foregoing embodiments it is also contemplated that the intercranial implant with universal power supply could be configured as an "off the shelf" item. That is, the implant need not be a custom cranial implant configured to conform to the particular shape and contour of the patient's skull. For example, the intercranial implant with universal power supply may be pre-configured to occupy a defined shape and space with the universal power supply contained within the implant. In this manner, a sterile universal power supply implant may be stocked ready for use in surgery with a functional neurosurgical device implant.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A low-profile intercranial device with universal power supply, comprising:
a static cranial implant made of a material allowing for imaging of the brain through the static cranial implant;
a universal power supply including a universal implantable power source with a power output profile standardized for use with, and a connector adapted for reversible connection to, a wide array of different functional neurosurgical implants, the universal implantable power source being selected from the group consisting of a lithium-ion battery, a solid-state battery, a microbiology battery, a glucose powered system, a piezoelectric battery, and a kinetic energy harvesting system;
wherein the static cranial implant includes a power supply recess adapted for the placement of the universal power supply within the static cranial implant.

2. The low-profile intercranial device with universal power supply according to claim 1, wherein the static cranial implant is adapted for the selective integration of a functional neurological implant.

3. The low-profile intercranial device with universal power supply according to claim 1, wherein the static cranial implant includes no encapsulated inner working.

4. The low-profile intercranial device with universal power supply according to claim 1, wherein the static cranial implant includes a cavity shaped and dimensioned for the functional neurosurgical implant.

5. The low-profile intercranial device with universal power supply according to claim 1, wherein the connector is a Lightning connector.

6. The low-profile intercranial device with universal power supply according to claim 1, wherein the connector is a USB connector.

7. The low-profile intercranial device with universal power supply according to claim 1, wherein the static cranial implant is fabricated from PMMA (Poly(methyl methacrylate)), PEEK (Polyether ether ketone), PEKK (Polyetherketoneketone), porous polyethylene, titanium alloy, bone allograft, bone autograft, bone xenograft, and/or various other tissue-engineered bone constructs.

8. The low-profile intercranial device with universal power supply according to claim 1, wherein the static cranial implant is fully lucent and transparent.

9. The low-profile intercranial device with universal power supply according to claim 1, wherein the static cranial implant is fully translucent to light, sonolucent to ultrasound, radiolucent to ECOG signals, and transparent for ideal visualization.

10. The low-profile intercranial device with universal power supply according to claim 1, wherein the static cranial implant comprises part of a multiple-part intercranial assembly.

11. The low-profile intercranial device with universal power supply according to claim 10, wherein the universal power supply is connected to a functional neurosurgical implant contained in a separate portion of the multiple-part intercranial assembly.

12. The low-profile intercranial device with universal power supply according to claim 1, wherein the universal power supply is configured to be connected to a functional neurosurgical implanted which is implantable directly in the brain.

* * * * *